US007872245B2

(12) United States Patent
Vaschenko et al.

(10) Patent No.: US 7,872,245 B2

(45) Date of Patent: Jan. 18, 2011

(54) SYSTEMS AND METHODS FOR TARGET MATERIAL DELIVERY IN A LASER PRODUCED PLASMA EUV LIGHT SOURCE

(75) Inventors: Georgiy O. Vaschenko, San Diego, CA (US); Alexander N. Bykanov, San Diego, CA (US); Norbert R. Bowering, Bielefeld (DE); David C. Brandt, Escondido, CA (US); Alexander I. Ershov, Escondido, CA (US); Rodney D. Simmons, San Diego, CA (US); Oleh V. Khodykin, San Diego, CA (US); Igor V. Fomenkov, San Diego, CA (US)

(73) Assignee: Cymer, Inc., San Diego, CA (US)

( * ) Notice: Subject to any disclaimer, the term of this patent is extended or adjusted under 35 U.S.C. 154(b) by 406 days.

(21) Appl. No.: 12/214,736

(22) Filed: Jun. 19, 2008

(65) Prior Publication Data

US 2009/0230326 A1 Sep. 17, 2009

Related U.S. Application Data

(60) Provisional application No. 61/069,818, filed on Mar. 17, 2008.

(51) Int. Cl.
*A61N 5/00* (2006.01)
*G21G 5/00* (2006.01)

(52) U.S. Cl. ............................... 250/492.2; 250/504 R; 250/493.1; 250/492.1; 250/354.1; 250/372; 250/503.1; 359/359; 359/333; 156/345.24; 156/345.5; 378/34

(58) Field of Classification Search .............. 250/492.2, 250/504 R, 493.1, 492.1, 354.1, 372, 503.1; 359/359, 333; 156/345.24, 345.5; 378/34
See application file for complete search history.

(56) References Cited

U.S. PATENT DOCUMENTS

| | | | | |
|---|---|---|---|---|
| 6,324,256 | B1 | 11/2001 | McGregor et al. | 378/119 |
| 6,398,374 | B1 | 6/2002 | Chapman et al. | 359/857 |
| 6,549,551 | B2 | 4/2003 | Partlo et al. | 372/38.07 |
| 6,567,450 | B2 | 5/2003 | Myers et al. | 372/55 |
| 6,625,191 | B2 | 9/2003 | Knowles et al. | 372/55 |
| 6,647,088 | B1 | 11/2003 | Schmidt et al. | 378/34 |

(Continued)

OTHER PUBLICATIONS

U.S. Appl. No. 11/827,803, filed Jul. 13, 2007, Vaschenko.

(Continued)

*Primary Examiner*—Jack I Berman
*Assistant Examiner*—Meenakshi S Sahu
(74) *Attorney, Agent, or Firm*—Mattthew K. Hillman

(57) ABSTRACT

Devices are disclosed herein which may comprise an EUV reflective optic having a surface of revolution that defines a rotation axis and a circular periphery. The optic may be positioned to incline the axis at a nonzero angle relative to a horizontal plane, and to establish a vertical projection of the periphery in the horizontal plane with the periphery projection bounding a region in the horizontal plane. The device may further comprise a system delivering target material, the system having a target material release point that is located in the horizontal plane and outside the region, bounded by the periphery projection and a system generating a laser beam for irradiating the target material to generate an EUV emission.

25 Claims, 12 Drawing Sheets

U.S. PATENT DOCUMENTS

| | | | | |
|---|---|---|---|---|
| 7,372,056 | B2 | 5/2008 | Bykanov et al. | 250/504 R |
| 7,378,673 | B2 | 5/2008 | Bykanov et al. | 250/503.1 |
| 7,405,416 | B2 | 7/2008 | Algots et al. | 250/493.1 |
| 2002/0136354 | A1 * | 9/2002 | Takenaka et al. | 378/84 |
| 2006/0120429 | A1 * | 6/2006 | Murakami | 372/107 |
| 2006/0131515 | A1 | 6/2006 | Partlo et al. | 250/504 R |
| 2006/0192153 | A1 * | 8/2006 | Bykanov et al. | 250/503.1 |
| 2006/0192155 | A1 * | 8/2006 | Algots et al. | 250/504 R |
| 2006/0249699 | A1 | 11/2006 | Bowering et al. | 250/504 R |
| 2006/0255298 | A1 | 11/2006 | Bykanov et al. | 250/504 R |
| 2007/0001131 | A1 | 1/2007 | Ershov et al. | 250/503.1 |
| 2007/0187627 | A1 * | 8/2007 | Ershov et al. | 250/504 R |
| 2008/0043321 | A1 | 2/2008 | Bowering et al. | 359/359 |
| 2008/0048133 | A1 * | 2/2008 | Bykanov et al. | 250/504 R |
| 2008/0087847 | A1 | 4/2008 | Bykanov et al. | 250/504 R |

OTHER PUBLICATIONS

PCT Search Report dated Jun. 16, 2009, PCT Application No. PCT/US2009/000994.

* cited by examiner

SYSTEMS AND METHODS FOR TARGET MATERIAL DELIVERY IN A LASER PRODUCED PLASMA EUV LIGHT SOURCE

The present application claims priority to co-pending U.S. Provisional Patent Application Ser. No. 61/069,818, entitled SYSTEMS AND METHODS FOR TARGET MATERIAL DELIVERY IN A LASER PRODUCED PLASMA EUV LIGHT SOURCE, filed on Mar. 17, 2008, the disclosure of which is hereby incorporated by reference herein.

FIELD

The present disclosure relates to extreme ultraviolet ("EUV") light sources that provide EUV light from a plasma that is created from a target material and collected and directed to an intermediate region for utilization outside of the EUV light source chamber, e.g., by a lithography scanner/stepper.

BACKGROUND

Extreme ultraviolet light, e.g., electromagnetic radiation having wavelengths of around 50 nm or less (also sometimes referred to as soft x-rays), and including light at a wavelength of about 13.5 nm, can be used in photolithography processes to produce extremely small features in substrates, e.g., silicon wafers.

For these processes, it is typically convenient to irradiate the flat workpiece, e.g., wafer, while the workpiece is oriented horizontally. Indeed, orienting the workpiece horizontally may facilitate handling and clamping of the workpiece. This workpiece orientation may then drive the orientations and positions of the scanner optics, e.g., projection optics, masks, conditioning optics, etc., and in some cases may establish a preferential orientation of the initial light beam generated by lithography tool's light source. It is, of course, also generally preferable to minimize the number of optics along the path between the light source and wafer, as each optic reduces light intensity and has the potential to introduce aberrations into the beam. With this in mind, it may happen that a light source which generates a beam of light at a substantial incline to the horizontal direction, is preferable in some instances.

Methods to produce a directed EUV light beam include, but are not necessarily limited to, converting a material into a plasma state that has at least one element, e.g., xenon, lithium or tin, with one or more emission lines in the EUV range. In one such method, often termed laser-produced-plasma ("LPP"), the required plasma can be produced by irradiating a target material having the required line-emitting element, with a laser beam.

One particular LPP technique involves generating a stream of target material droplets and irradiating some or all of the droplets with laser light pulses, e.g. zero, one or more pre-pulse(s) followed by a main pulse. In more theoretical terms, LPP light sources generate EUV radiation by depositing laser energy into a target material having at least one EUV emitting element, such as xenon (Xe), tin (Sn) or lithium (Li), creating a highly ionized plasma with electron temperatures of several 10's of eV. The energetic radiation generated during de-excitation and recombination of these ions is emitted from the plasma in all directions. In one common arrangement, a near-normal-incidence mirror (often termed a "collector mirror") is positioned at a relatively short distance, e.g., 10-50 cm, from the plasma to collect, direct (and in some arrangements, focus) the light to an intermediate location, e.g., a focal point. The collected light may then be relayed from the intermediate location to a set of scanner optics and ultimately to a wafer. To efficiently reflect EUV light at near normal incidence, a mirror having a delicate and relatively expensive multi-layer coating is typically employed. Keeping the surface of the collector mirror clean and protecting the surface from plasma-generated debris has been one of the major challenges facing the EUV light source developers.

In quantitative terms, one arrangement that is currently being developed with the goal of producing about 100 W at the intermediate location contemplates the use of a pulsed, focused 10-12 kW $CO_2$ drive laser which is synchronized with a droplet generator to sequentially irradiate about 10,000-200,000 tin droplets per second. For this purpose, there is a need to produce a stable stream of droplets at a relatively high repetition rate (e.g., 10-200 kHz or more) and deliver the droplets to an irradiation site with high accuracy and good repeatability in terms of timing and position over relatively long periods of time.

In one previously disclosed arrangement, a substantially vertical stream of droplets is generated and directed to pass through one of the two foci of a collector mirror shaped as a prolate spheroid (i.e., a portion of an ellipse rotated about its major axis). With the vertical stream, the mirror may be positioned out of the path of the droplets. However, with this positioning, a cone-shaped EUV output beam is generated that is aligned along or near the horizontal direction. As indicated above, it may be desirable in some circumstances to produce an EUV source output beam that is substantially inclined relative to the horizontal direction.

Additionally, vertically-oriented droplet streams and the supporting devices may result in vertically-oriented obscurations of the beam path between the collector mirror and the workpiece, e.g. wafer. For some scanner designs non-vertical obscurations may be favored over vertically-oriented obscurations for one or more reasons such as to align the droplet related obscuration with a pre-existing scanner obscuration and/or to produce an obscuration aligned relative to the scan direction which will create an intensity variation at the wafer which 'averages out' over a scan and can be compensated by dose adjustment.

With the above in mind, applicants disclose systems and methods for target material delivery in a laser produced plasma EUV light source, and corresponding methods of use.

SUMMARY

In one aspect, a device is disclosed which may comprise an EUV reflective optic having a surface of revolution that defines a rotation axis and a circular periphery. The optic may be positioned to incline the axis at a nonzero angle relative to a horizontal plane and to establish a vertical projection of the periphery in the horizontal plane with the periphery projection bounding a region in the horizontal plane. The device may further comprise a system delivering target material, the system having a target material release point that is located in the horizontal plane and outside the region bounded by the periphery projection and a system generating a laser beam for irradiating the target material to generate an EUV emission.

In one embodiment of this aspect, the surface of revolution may be a rotated ellipse, the ellipse defining a pair of foci and being rotated about the ellipses axis passing through each focus.

In another aspect, a device is disclosed which may comprise a source of target material droplets delivering target material to an irradiation region along a non-vertical path between the irradiation region and a target material release point; an EUV reflective optic; a laser producing a beam irradiating the droplets at the irradiation region to generate a plasma producing EUV radiation; and a catch positioned to receive target material to protect the reflective optic.

In one embodiment the catch may comprise a tube, and in a particular embodiment, the irradiation region may be located in the tube, and the tube may be formed with an orifice to pass the EUV radiation from the irradiation region to the reflective optic. An in-situ mechanism may be provided for moving the tube from a position where the tube is located along the path to a position where the tube does not obstruct EUV light reflected from the EUV reflective optic.

In one arrangement, the tube may be a shield protecting the reflective optic from target material straying from the non-vertical path. In one setup, the tube may extend from a location wherein the tube at least partially surrounds the target material release point to a tube terminus positioned between the release point and the irradiation region.

In one implementation, the catch may comprise a retractable cover extendable over an operable surface of the reflective optic.

In another embodiment of this aspect, the catch may comprise a structure positioned to receive target material that has passed through the irradiation region and prevent received material from splashing and reaching the reflective optic. For example, the structure may comprise an elongated tube.

In another aspect, a source material dispenser for an EUV light source is to disclosed which may comprise a source material conduit having a wall and formed with an orifice; a conductive coating deposited on the wall; an insulating coating deposited on the conductive coating; a source passing electrical current through the conductive coating to produce heat; and an electro-actuatable element contacting the insulating coating and operable to deform the wall and modulate a release of source material from the dispenser.

In one arrangement, the conduit may comprise a tube and in a particular arrangement, the tube may be made of glass and the conductive coating may comprise a nickel-cobalt-ferrous alloy.

In one embodiment of this aspect, the insulating coating may comprise a metal oxide.

For the source material dispenser, the electro-actuatable element may be made of a piezoelectric material, an electrostrictive material or a magnetostrictive material.

For this aspect, the source material comprises liquid Sn.

In another aspect, a source material dispenser for an EUV light source is disclosed which may comprise a source material conduit comprising a tubular glass portion having a coefficient of thermal expansion ($CTE_{glass}$) and a metal coupled to the glass portion, the metal having a coefficient of thermal expansion ($CTE_{metal}$) which differs from $CTE_{glass}$ by less than 5 ppm/degree Celsius over the range of temperatures of 25 to 250 degrees Celsius.

In one embodiment, the joining metal may comprise a nickel-cobalt-ferrous alloy and in another embodiment, the metal may comprise molybdenum.

In another aspect, a source material dispenser producing source material droplets for an EUV light source is disclosed which may comprise a source material conduit having a source material receiving end and a source material exit end; and a confining structure restricting movement of the source material exit end of the conduit to reduce droplet stream instabilities.

In a particular embodiment, the source material may comprise a molten material heated above twenty five degrees Celsius, e.g. liquid tin or lithium, and the confining structure may comprise a rigid member sized to provide a gap between the conduit and member at the operating temperature of the conduit.

In one setup, the member may be a ferrule made of a material having a coefficient of thermal expansion ($CTE_{ferrule}$) and the conduit may be made of a material having a coefficient of thermal expansion ($CTE_{conduit}$) such that a gap distance between the ferrule and conduit decreases with increasing temperature, and in another setup, the member may be a ferrule made of a material having a coefficient of thermal expansion ($CTE_{ferrule}$), the conduit is made of a material having a coefficient of thermal expansion ($CTE_{conduit}$) such that a gap distance between the ferrule and conduit increases with increasing temperature.

In another embodiment, the confining structure may comprise a flexible ferrule sized to be in contact with the conduit at the operating temperature of the conduit.

BRIEF DESCRIPTION OF THE DRAWINGS

FIGS. 7 and 9 are side plan views, FIG. 8 shows a sectional view as seen along line 8-8 in FIG. 7, and FIG. 10 shows a sectional view as seen along line 10-10 in FIG. 9;

DETAILED DESCRIPTION

Figure 1:
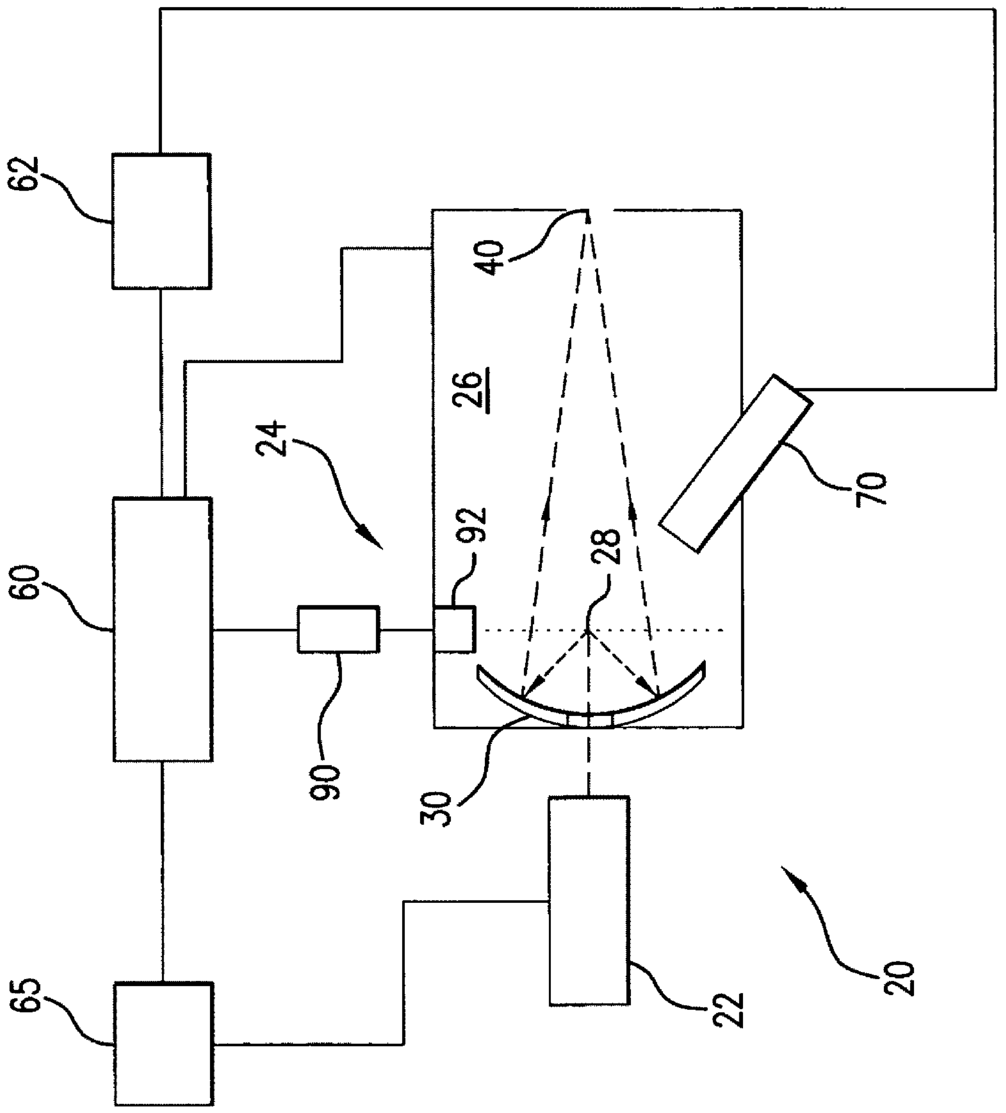
FIG. 1 shows a simplified, schematic view of a laser produced plasma EUV light source.

With initial reference to FIG. 1, there is shown a schematic view of an EUV light source, e.g., a laser-produced-plasma EUV light source 20, according to one aspect of an embodiment. As shown in FIG. 1, and described in further detail below, the LPP light source 20 may include a system 22 for generating a train of light pulses and delivering the light pulses into a chamber 26. As detailed below, each light pulse may travel along a beam path from the system 22 and into the chamber 26 to illuminate a respective target droplet at an irradiation region 28.

Suitable lasers for use in the system 22 shown in FIG. 1, may include a pulsed laser device, e.g., a pulsed gas discharge $CO_2$ laser device producing radiation at 9.3 μm or 10.6 μm, e.g., with DC or RF excitation, operating at relatively high power, e.g., 10 kW or higher and high pulse repetition rate, e.g., 50 kHz or more. In one particular implementation, the laser may be an axial-flow RF-pumped $CO_2$ laser having a MOPA configuration with multiple stages of amplification and having a seed pulse that is initiated by a Q-switched Master Oscillator (MO) with low energy and high repetition rate, e.g., capable of 100 kHz operation. From the MO, the laser pulse may then be amplified, shaped, and focused before reaching the irradiation region 28. Continuously pumped $CO_2$ amplifiers may be used for the system 22. For example, a suitable $CO_2$ laser device having an oscillator and three amplifiers (O-PA1-PA2-PA3 configuration) is disclosed in co-pending U.S. patent application Ser. No. 11/174,299 filed on Jun. 29, 2005, entitled, LPP EUV LIGHT SOURCE DRIVE LASER SYSTEM, the entire contents of which are hereby incorporated by reference herein. Alternatively, the laser may be configured as a so-called "self-targeting" laser system in which the droplet serves as one mirror of the optical cavity. In some "self-targeting" arrangements, a master oscillator may not be required. Self targeting laser systems are disclosed and claimed in co-pending U.S. patent application Ser. No. 11/580,414 filed on Oct. 13, 2006, entitled, DRIVE LASER DELIVERY SYSTEMS FOR EUV LIGHT SOURCE, the entire contents of which are hereby incorporated by reference herein.

Depending on the application, other types of lasers may also be suitable, e.g., an excimer or molecular fluorine laser operating at high power and high pulse repetition rate. Other examples include, a solid state laser, e.g., having a fiber, rod or disk shaped active media, a MOPA configured excimer laser system, e.g., as shown in U.S. Pat. Nos. 6,625,191, 6,549,551, and 6,567,450, the entire contents of which are hereby incorporated by reference herein, an excimer laser having one or more chambers, e.g., an oscillator chamber and one or more amplifying chambers (with the amplifying chambers in parallel or in series), a master oscillator/power oscillator (MOPO) arrangement, a master oscillator/power ring amplifier (MOPRA) arrangement, a power oscillator/power amplifier (POPA) arrangement, or a solid state laser that seeds one or more excimer or molecular fluorine amplifier or oscillator chambers, may be suitable. Other designs are possible.

As further shown in FIG. 1, the EUV light source 20 may also include a target material delivery system 24, e.g., delivering droplets of a target material into the interior of a chamber 26 to the irradiation region 28, where the droplets will interact with one or more light pulses, e.g., one or more pre-pulses and thereafter one or more main pulses, to ultimately produce a plasma and generate an EUV emission. The target material may include, but is not necessarily limited to, a material that includes tin, lithium, xenon or combinations thereof. The EUV emitting element, e.g., tin, lithium, xenon, etc., may be in the form of liquid droplets and/or solid particles contained within liquid droplets. For example, the element tin may be used as pure tin, as a tin compound, e.g., $SnBr_4$, $SnBr_2$, $SnH_4$, as a tin alloy, e.g., tin-gallium alloys, tin-indium alloys, tin-indium-gallium alloys, or a combination thereof. Depending on the material used, the target material may be presented to the irradiation region 28 at various temperatures including room temperature or near room temperature (e.g., tin alloys, $SnBr_4$), at an elevated temperature, (e.g., pure tin) or at temperatures below room temperature, (e.g., $SnH_4$), and in some cases, can be relatively volatile, e.g., $SnBr_4$. More details concerning the use of these materials in an LPP EUV light source is provided in co-pending U.S. patent application Ser. No. 11/406,216, filed on Apr. 17, 2006, entitled ALTERNATIVE FUELS FOR EUV LIGHT SOURCE, the contents of which are hereby incorporated by reference herein.

Continuing with FIG. 1, the EUV light source 20 may also include an optic 30, e.g., a near-normal incidence collector mirror having a reflective surface in the form of a prolate spheroid (i.e., an ellipse rotated about its major axis) having, e.g., a graded multi-layer coating with alternating layers of Molybdenum and Silicon, and in some cases one or more high temperature diffusion barrier layers, smoothing layers, capping layers and/or etch stop layers. FIG. 1 shows that the optic 30 may be formed with an aperture to allow the light pulses generated by the system 22 to pass through and reach the irradiation region 28. As shown, the optic 30 may be, e.g., a prolate spheroid mirror that has a first focus within or near the irradiation region 28 and a second focus at a so-called intermediate region 40, where the EUV light may be output from the EUV light source 20 and input to a device utilizing EUV light, e.g., an integrated circuit lithography tool (not shown). It is to be appreciated that other optics may be used in place of the prolate spheroid mirror for collecting and directing light to an intermediate location for subsequent delivery to a device utilizing EUV light, for example the optic may be a parabola rotated about its major axis or may be configured to deliver a beam having a ring-shaped cross-section to an intermediate location, see e.g., co-pending U.S. patent application Ser. No. 11/505,177, filed on Aug. 16, 2006, entitled EUV OPTICS, the contents of which are hereby incorporated by reference.

Continuing with reference to FIG. 1, the EUV light source 20 may also include an EUV controller 60, which may also include a firing control system 65 for triggering one or more lamps and/or laser devices in the system 22 to thereby generate light pulses for delivery into the chamber 26. The EUV light source 20 may also include a droplet position detection system which may include one or more droplet imagers 70 e.g., system(s) for capturing images using CCD's and/or backlight stroboscopic illumination and/or light curtains that provide an output indicative of the position and/or timing of one or more droplets, e.g., relative to the irradiation region 28. The imager(s) 70 may provide this output to a droplet position detection feedback system 62, which can, e.g., compute a droplet position and trajectory, from which a droplet error can be computed, e.g., on a droplet by droplet basis or on average. The droplet position error may then be provided as an input to the controller 60, which can, for example, provide a position, direction and/or timing correction signal to the system 22 to control a source timing circuit and/or to control a beam position and shaping system, e.g., to change the trajectory and/or focal power of the light pulses being delivered to the irradiation region 28 in the chamber 26.

The EUV light source 20 may include one or more EUV metrology instruments for measuring various properties of the EUV light generated by the source 20. These properties may include, for example, intensity (e.g., total intensity or intensity within a particular spectral band), spectral bandwidth, polarization, beam position, pointing, etc. For the EUV light source 20, the instrument(s) may be configured to operate while the downstream tool, e.g., photolithography scanner, is on-line, e.g., by sampling a portion of the EUV output, e.g., using a pickoff mirror or sampling "uncollected" EUV light, and/or may operate while the downstream tool, e.g., photolithography scanner, is off-line, for example, by measuring the entire EUV output of the EUV light source 20.

As further shown in FIG. 1, the EUV light source 20 may include a droplet control system 90, operable in response to a signal (which in some implementations may include the droplet error described above, or some quantity derived therefrom) from the controller 60, to e.g., modify the release point of the target material from a source material dispenser 92 and/or modify droplet formation timing, to correct for errors in the droplets arriving at the desired irradiation region 28 and/or synchronize the generation of droplets with the pulsed laser system 22.

Figure 2:
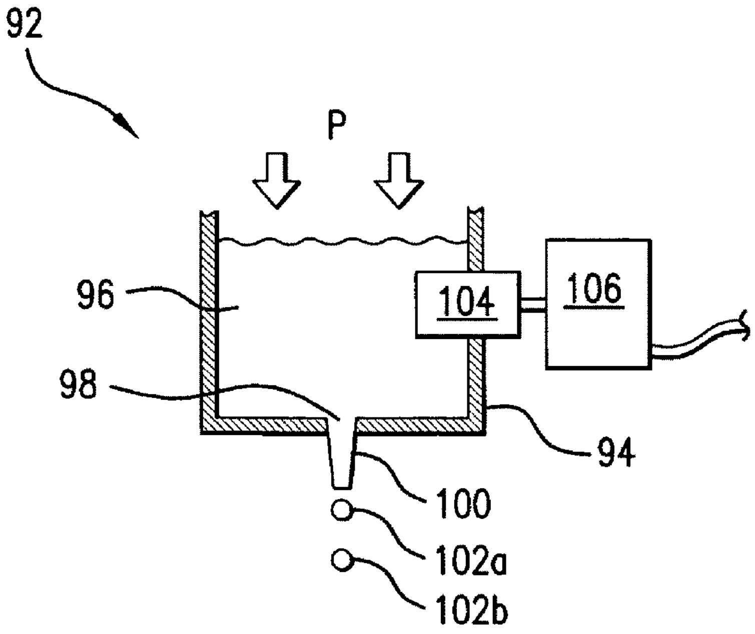
FIG. 2 shows a schematic, sectional view a simplified droplet source.
Figure 2A:
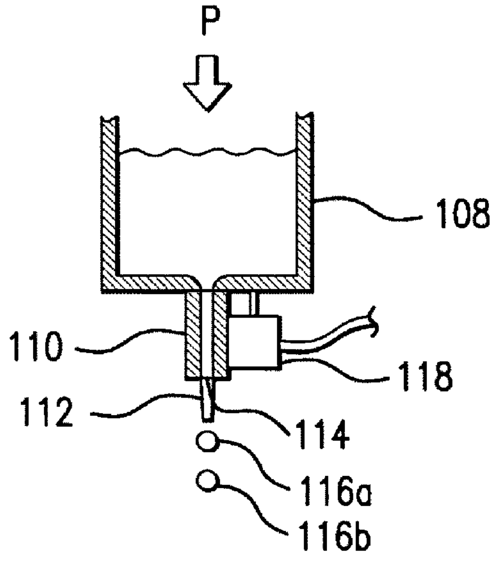
FIGS. 2A-2D show sectional views illustrating several different techniques for coupling an electro-actuatable element with a fluid to create a disturbance in a stream exiting an orifice.

FIG. 2 illustrates in schematic format the components of a simplified source material dispenser 92 that may be used in some or all of the embodiments described herein. As shown there, the source material dispenser 92 may include a conduit, which for the case shown is a reservoir 94 holding a fluid 96, e.g., molten tin, under pressure, P. Also shown, the reservoir 94 may be formed with an orifice 98 allowing the pressurized fluid 96 to flow through the orifice establishing a continuous stream 100 which subsequently breaks into a plurality of droplets 102*a, b*.

Figure 2B:
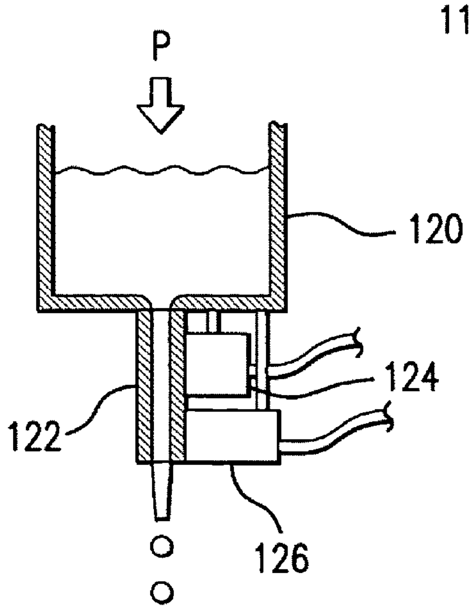
Figure 2C:
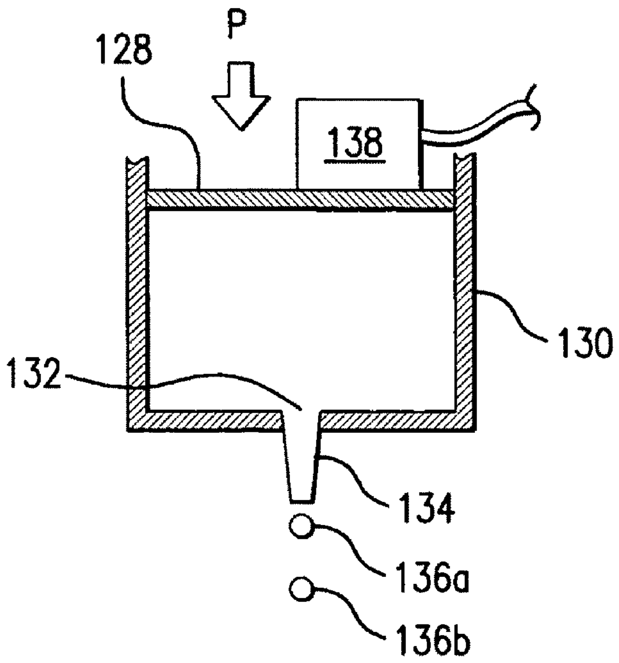
Figure 2D:
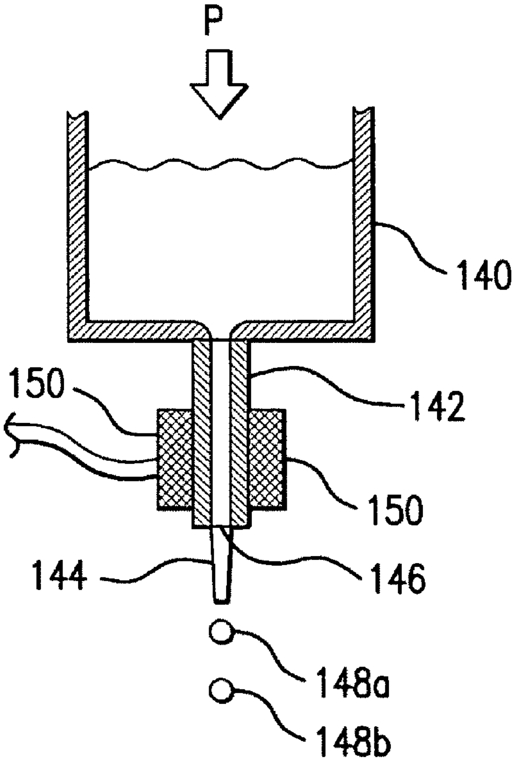

Continuing with FIG. 2, the source material dispenser 92 further includes a sub-system producing a disturbance in the fluid having an electro-actuatable element 104 that is operable, coupled with the fluid 98 and a signal generator 106 driving the electro-actuatable element 104. FIGS. 2A-2D show various ways in which one or more electro-actuatable elements may be operable coupled with the fluid to create droplets. The coupling techniques shown in FIGS. 2A-2D may be used in some or all of the embodiments described herein. Beginning with FIG. 2A, an arrangement is shown in which the fluid is forced to flow from a reservoir 108 under pressure through a conduit 110, e.g., capillary tube, having a relatively small diameter and a length of about 10 to 50 mm, creating a continuous stream 112 exiting an orifice 114 of the conduit 110, which subsequently breaks up into droplets 116*a,b*. As shown, an electro-actuatable element 118 may be coupled to the conduit. For example, an electro-actuatable element may be coupled to the conduit 110 to deflect the conduit 110 and disturb the stream 112. FIG. 2B shows a similar arrangement having a reservoir 120, conduit 122 and a pair of electro-actuatable elements 124, 126, each coupled to the conduit 122, to deflect the conduit 122 at a respective frequency. FIG. 2C shows another variation in which a plate 128 is positioned in a reservoir conduit 130, moveable to force fluid through an orifice 132 to create a stream 134 which breaks into droplets 136*a,b*. As shown, a force may be applied to the plate 128, and one or more electro-actuatable elements 138 may be coupled to the plate to disturb the stream 134. It is to be appreciated that a capillary tube may be used with the embodiment shown in FIG. 2C. FIG. 2D shows another variation in which a fluid is forced to flow from a reservoir 140 under pressure through a conduit 142 creating a continuous stream 144 exiting an orifice 146 of the conduit 142, which subsequently breaks up into droplets 148*a,b*. As shown, an electro-actuatable element 150, e.g., having a ring-like or tube-like shape, may be positioned around the tube 142. When driven, the electro-actuatable element 142 may selectively squeeze the conduit 142 to disturb the stream 144. It is to be appreciated that two or more electro-actuatable elements may be employed to selectively squeeze the conduit 142 at respective frequencies.

More details regarding various droplet dispenser configurations and their relative advantages may be found in co-pending U.S. patent application Ser. No. 11/827,803, filed on Jul. 13, 2007, entitled LASER PRODUCED PLASMA EUV LIGHT SOURCE HAVING A DROPLET STREAM PRODUCED USING A MODULATED DISTURBANCE WAVE; co-pending U.S. patent application Ser. No. 11/358,988, filed on Feb. 21, 2006, entitled LASER PRODUCED PLASMA EUV LIGHT SOURCE WITH PRE-PULSE; co-pending U.S. patent application Ser. No. 11/067,124, filed on Feb. 25, 2005, entitled METHOD AND APPARATUS FOR EUV PLASMA SOURCE TARGET DELIVERY; and co-pending U.S. patent application Ser. No. 11/174,443, filed on Jun. 29, 2005, entitled LPP EUV PLASMA SOURCE MATERIAL TARGET DELIVERY SYSTEM; the contents of each of which are hereby incorporated by reference.

Figure 3:
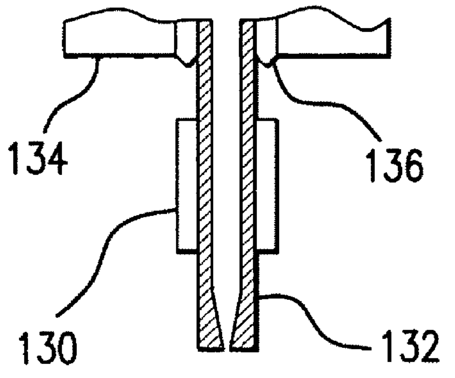
FIG. 3 shows a sectional view of portions of a source material dispenser for an EUV light source having a source material conduit including a joining metal coupling a borosilicate glass portion and a metallic portion, the joining metal selected to have a coefficient of thermal expansion closely matching the coefficient of thermal expansion of the borosilicate glass.

FIG. 3 shows portions of a source material dispenser for an EUV light source having a source material conduit that includes an electro-actuatable element 130, glass portion 132, e.g. a silica based glass such as borosilicate glass or quartz, and a metallic portion 134, shown as a flange. For example, the glass portion 132 may be a glass capillary tube having a shaped exit orifice nozzle. As shown, the dispenser further includes a sealing joint 136 consisting of a joining metal coupling the glass portion and the metallic portion.

For this arrangement, the joining metal is selected to have a coefficient of thermal expansion ($CTE_{metal}$) closely matching the coefficient of thermal expansion of the glass ($CTE_{glass}$) over the operational temperature range, e.g. 25-260 degrees Celsius for liquid tin as a target material. In some cases, a tubular glass portion having a coefficient of thermal expansion ($CTE_{glass}$) is used with a metal coupled to the glass portion, the metal having a coefficient of thermal expansion ($CTE_{metal}$) which differs from $CTE_{glass}$ by less than 5 ppm/degree Celsius over the range of temperatures of 25 to 260 degrees Celsius. In addition to glass-Kovar and glass-Mo, other combinations having a CTE difference of less than 5 ppm/degree Celsius over the range of temperatures of 25 to 250 degrees Celsius include invar/quartz, molybdenum/aluminum, Kovar/aluminum, platinum/soda-lime glass, molybdenum/quartz, tungsten/borosilicate glass, and stainless steel/alkali barium glass (Corning 9010).

For example, the joining metal may consist of a nickel-cobalt-ferrous alloy, such as Kovar, or the joining metal may consist of a molybdenum or tungsten. With this arrangement, cracking of the glass capillary after heating up the nozzle to a working temperature, e.g., (250-260 C for operation with molten tin) may be avoided.

As used herein, the name Kovar is employed as a general term for FeNi alloys having particular thermal expansion properties, and includes nickel-cobalt ferrous alloys designed to be compatible with the thermal expansion characteristics of borosilicate glass (~$5\times10^{-6}$/° C. between 30 and 200° C., to ~$10\times10^{-6}$/° C. at 800° C.), allowing direct mechanical connections over a range of temperatures. One particular Kovar alloy is composed of about 29% nickel, 17% cobalt, 0.2% silicon, 0.3% manganese, and 53.5% iron (by weight).

Figure 3A:
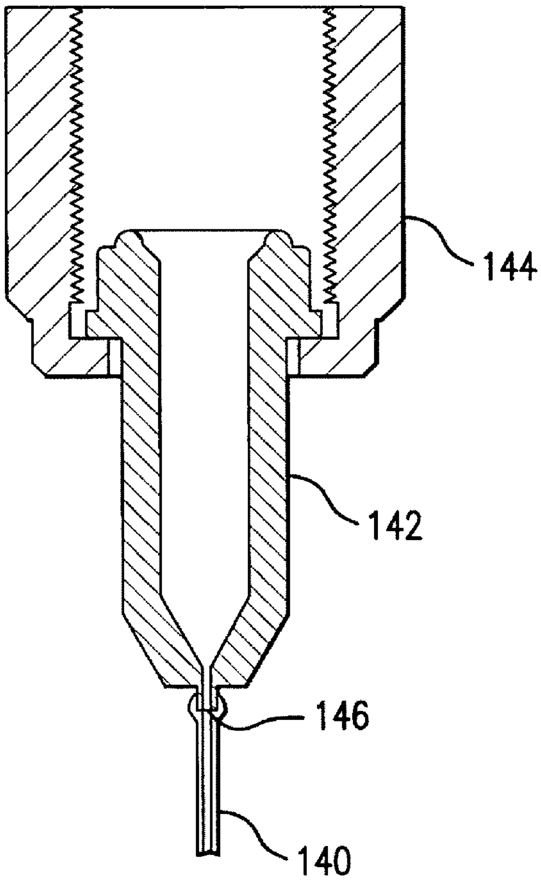
FIGS. 3A-F show sectional views of portions of source material dispensers for an EUV light source having a source material conduit that includes a borosilicate glass portion illustrating various techniques for coupling the glass portion to a non-glass portion.

FIG. 3A shows portions of a source material dispenser for an EUV light source having a source material conduit that includes a borosilicate glass portion 140, e.g. a glass capillary tube and a portion 142, shown as a face seal, e.g. VCR seal component, and a nut 144 used to clamp and seal the open face seal, e.g. VCR seal component to another face seal, e.g. VCR seal component (not shown). For the arrangement shown in FIG. 3A, the portion 142, e.g., open face seal, e.g. VCR seal component may be made of a material that is selected to have a coefficient of thermal expansion ($CTE_{metal}$) closely matching the coefficient of thermal expansion of the glass ($CTE_{glass}$). For example, the material may consist of a nickel-cobalt-ferrous alloy, such as Kovar, or the material may consist of molybdenum or tungsten. With this arrangement, cracking of the glass capillary after heating-up the nozzle to a working temperature, e.g., (250-260 C for operation with molten tin) may be avoided. For the arrangement shown in FIG. 3A, the portion 142 may be formed with a circular, hollow protrusion 146 extending from the body of portion 142 and allowing the capillary tube (glass portion 140) to slide over and attach to the protrusion. In one implementation, the arrangement shown in FIG. 3A may be prepared by heating the end of the glass capillary to approximately 1100 to 1700 degrees C. and holding it in the position shown until the capillary cools.

FIGS. 3B-3F show examples of other arrangements for coupling a glass portion, e.g., a glass capillary tube, and an open face seal, e.g. VCR seal component, where, as described above, the open face seal, e.g. VCR seal component may be made of a material that is selected to have a coefficient of thermal expansion ($CTE_{metal}$) closely matching the coefficient of thermal expansion of the glass ($CTE_{glass}$). For example, the material may consist of a nickel-cobalt-ferrous alloy, molybdenum, or tungsten.

Figure 3B:
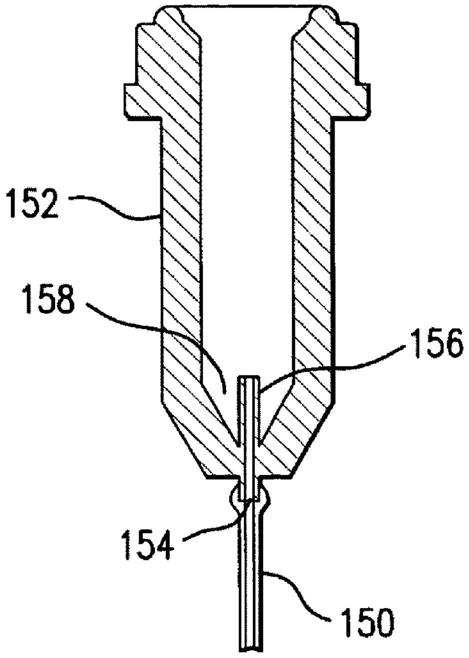

In more detail, FIG. 3B shows portions of a source material dispenser for an EUV light source having a source material conduit that includes a glass portion 150, e.g., a glass capillary tube coupled to conduit portion 152, shown as an open face seal, e.g. VCR seal component, using the same arrangement shown in FIG. 3 and described above (i.e., the portion 152 may be formed with a circular, hollow protrusion 154 extending from the body of portion 152 and allowing the capillary tube (glass portion 150 to slide over and attach to the protrusion). In addition, as shown, the portion 152 may be formed with a circular, hollow internal protrusion 156 extending part way into the body of portion 152, and establish a trap region 158 which may be useful in trapping impurities (which may otherwise clog the relatively small capillary exit orifice, e.g., solids) as liquid source material, e.g., tin, flows from the portion 152 into the portion 150.

Figure 3C:
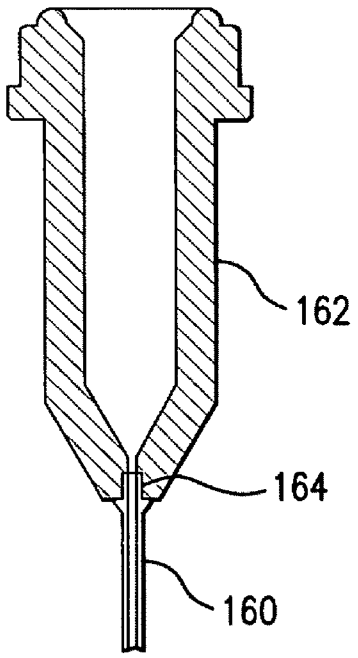

FIG. 3C shows portions of a source material dispenser for an EUV light source having a source material conduit that includes a glass portion 160, e.g., a glass capillary tube coupled to conduit portion 162, shown as an open face seal, e.g. VCR seal component, in which the conduit portion 162 may be formed with a circular recess 164 located in the output orifice of the conduit portion 162 and sized to allow one end of the capillary tube (glass portion 160) to slide into the recess and attach to the circular wall of the recess.

Figure 3D:
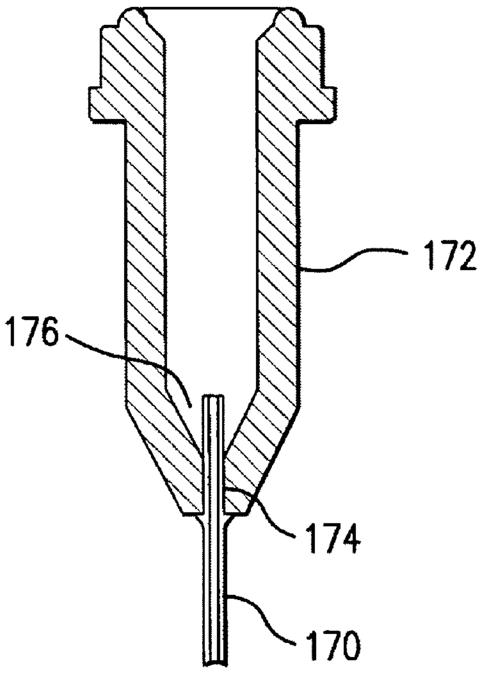

FIG. 3D shows portions of a source material dispenser for an EUV light source having a source material conduit that includes a glass portion 170, e.g. a glass capillary tube coupled to conduit portion 172, shown as an open face seal, e.g. VCR seal component, in which the portion 172 may be formed with a circular output orifice 174 sized to allow one end of the capillary tube (glass portion 170) to slide through output orifice 174 and into the body of the portion 172, attaching to the circular wall of the output orifice 174 and establishing an impurity trap 176 (as described above with reference to FIG. 3B).

Figure 3E:
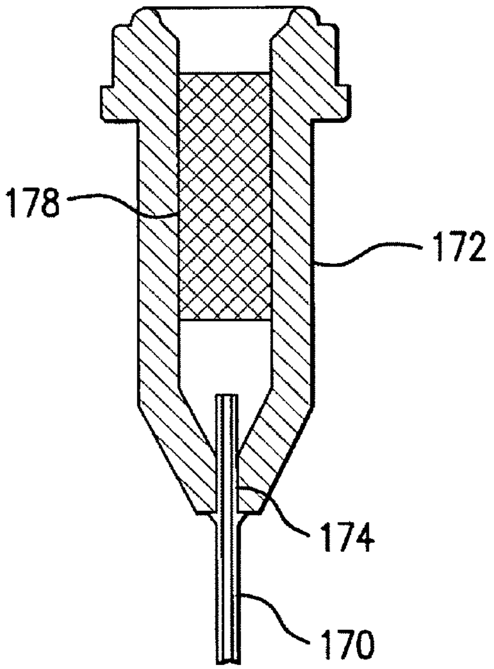

FIG. 3E shows portions of a source material dispenser for an EUV light source having one or more components in common with the arrangement shown in FIG. 3D, including a glass portion 170, conduit portion 172 formed with a circular output orifice 174, and further including a porous filter 178, e.g., made of sintered metal, woven metal and/or graphite fibers, disposed in the body of conduit portion 172 to remove impurities, e.g., solids, which may otherwise clog the capillary exit orifice. It is to be appreciated that the filter 178 may be incorporated in the other embodiments shown, e.g., FIGS. 3, 3A-C.

Figure 3F:
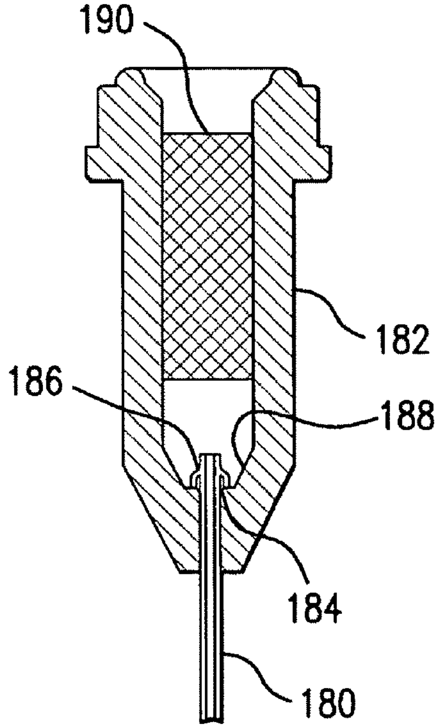

FIG. 3F shows portions of a source material dispenser for an EUV light source having a source material conduit that includes a borosilicate glass portion 180, e.g., a glass capillary tube coupled to conduit portion 182, shown as an open face seal, e.g. VCR seal component, in which the conduit portion 182 may be formed with a circular output orifice 184 sized to allow one end of the capillary tube (glass portion 180) to slide through output orifice 184 and into the body of the portion 182, attaching to the circular wall of the output orifice 184. As shown, the end of the glass portion 180 may be formed with an abutment 186 for attachment against the inner wall 188 of the portion 182. Also, shown, a filter 190, as described above with reference to FIG. 3E, may be used.

Figure 4:
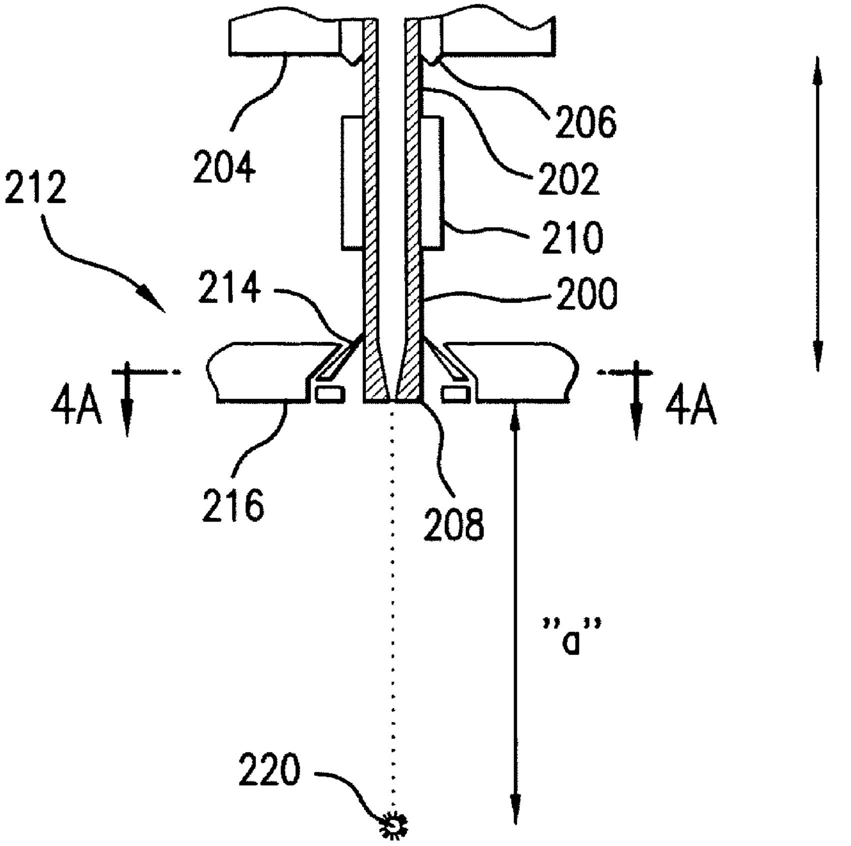
FIG. 4 shows portions of a source material dispenser producing source material droplets for an EUV light source having a confining structure restricting movement of the source material exit end to reduce droplet stream instabilities.

FIG. 4 shows portions of a source material dispenser producing source material droplets for an EUV light source including a source material conduit, which, for the case shown, includes a glass capillary tube 200 having a source material receiving end 202 that is rigidly affixed to dispenser portion 204, e.g., flange or open face seal, e.g. VCR seal component. This affixment may be achieved by brazing, bonding, e.g., epoxying, use of a CTE matched joining metal 206 (see FIG. 3 and corresponding description provided above), or by one of the coupling arrangements shown in FIGS. 3A-3F and described above. FIG. 4 also shows that the capillary tube 200 is formed with a source material exit end 208, and that the dispenser may include an electro-actuatable element 210, e.g., PZT, and a confining structure 212 restricting movement of the source material exit end 208, to reduce droplet stream instabilities. For example, the capillary tube 200 may have a length, "b" of about 10-50 mm. In the absence of a confining structure 212, the free end 208, may cause the nozzle to vibrate, and this vibration may cause instabilities of the droplet stream.

Figure 4A:
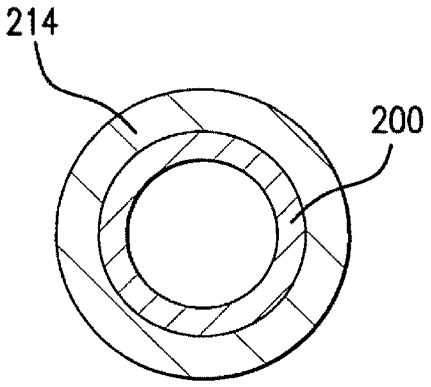
FIGS. 4A-B show sectional views as seen along line 4A-4A in FIG. 4 illustrating a rigid ferrule 214 that is sized such that it contacts the outer surface of the capillary tube when the capillary tube is at room temperature (FIG. 4A) and expands to establish a gap between the rigid ferrule and capillary tube at elevated temperatures, e.g. operating temperature (FIG. 4B)
Figure 4B:
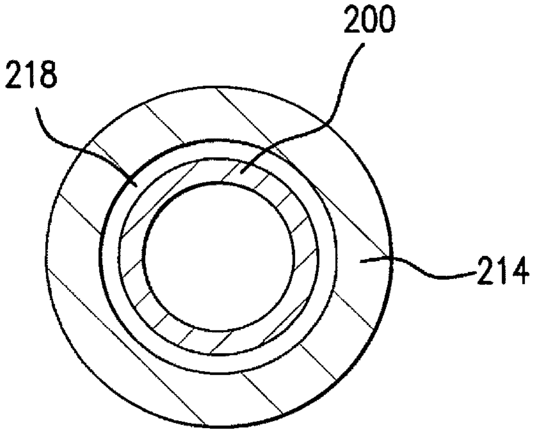

As shown in FIG. 4, the confining structure may include a ring shaped ferrule 214 and mount assembly 216. For elevated temperature source materials, e.g., liquid tin or lithium, the confining structure may employ a rigid ferrule as shown in FIGS. 4, 4A and 4B. In one design, the rigid ferrule 214 may be sized such that it contacts the outer surface of the capillary tube 200 when the capillary tube 200 is unheated, e.g., at room temperature, as shown in FIG. 4A. When capillary tube 200 reaches the operating temperature, e.g. ~250-260° C., a small gap 218 is established between the rigid ferrule 214 and capillary tube 200, as shown in FIG. 4B.

For example, glass has a typical CTE of 8-10 ppm/° C., the CTE of 300-series stainless steel is in the range 14 to 19 ppm/° C., and that of 400-series stainless is between 10 and 12 ppm/° C. Thus, there may be about 10 ppm/° C. CTE mismatch. For a typical capillary tube diameter of 1 mm and ~250° C. temperature change, a maximum material displacement caused by CTE mismatch can be:

1 mm*10 ppm/C*250 C=2.5 microns

Thus, there will be up to 2.5 micron gap between the rigid ferrule 214 and capillary tube 200. This gap will cause droplet stream instability at the target proportional to the ratio of (a+b)/b, where "a" is the distance between the capillary tube 200 and the irradiation region 220, and "b" is the length of the capillary tube. For example, if the capillary tube is one-inch and the distance between the capillary tube 200 and the irradiation region 220 is two-inches, the 2.5 micron gap will allow only about 7.5 micron droplet displacement at plasma. This may be acceptable since it is much smaller than the LPP laser beam size, which may be, for example, about 100-150 microns.

Figure 4C:
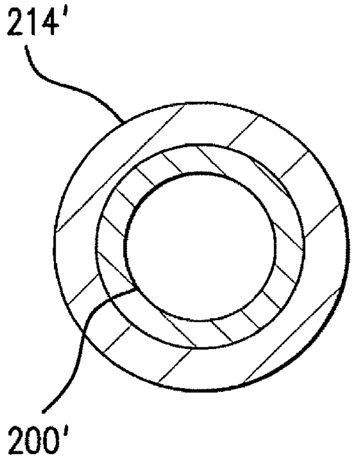
FIG. 4C shows a sectional view as seen along line 4A-4A in FIG. 4 illustrating a confining structure having a flexible ferrule sized to be in contact with the capillary tube at an elevated operating temperature.

FIG. 4C illustrates another embodiment in which the confining structure may comprise a flexible ferrule 214' e.g., a ferrule made of a compliant material, sized to be in contact with the conduit, e.g., capillary 200', at the operating temperature e.g., ~250-260° C. when liquid tin is used as a source material. For this arrangement, the flexible ferrule 214' may be sized to slightly squeeze the capillary tube 200' (below its breakage point) when it is cold, e.g. at room temperature. When the capillary tube 200 is hot, the flexible ferrule will still contact and hold the capillary tight. With this arrangement, there is no gap, but the capillary tube 200' may be spring loaded. In one implementation, the spring load can be made stiffer than the stiffness of the capillary tube 200' itself, such that the resonance frequency of the constrained capillary tube 200' is significantly higher than that of a free-hanging capillary.

Figure 4D:
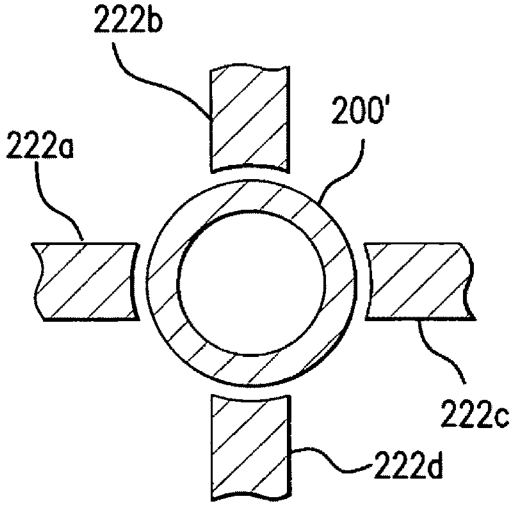
FIG. 4D shows a sectional view as seen along line 4A-4A in FIG. 4 illustrating another embodiment in which the confining structure may comprise four members arranged and positioned relative to the capillary tube to restrict movement of the source material exit end to reduce droplet stream instabilities.

FIG. 4D shows another embodiment in which the confining structure may comprise a plurality (in this case four) of members 222*a-d* arranged and positioned relative to the capillary tube 200" to restrict movement of the source material exit end (see FIG. 4) to reduce droplet stream instabilities. For elevated temperature source materials, e.g., liquid tin or lithium, the members 222*a-d* may be designed to expand to establish a pre-determined gap between the respective member and the capillary tube 200" at a selected operational temperature or one, some or all of the members 222*a-d* may be designed to expand to contact and apply a selected force on the capillary tube 200" at a selected operational temperature.

Also, alternatively, better CTE matching materials can be used to reduce the gap in case of a rigid ferrule, such as 400-stainless and glass or even better matching materials, e.g., the ferrule may be made of Kovar or Molybdenum.

Figure 5A:
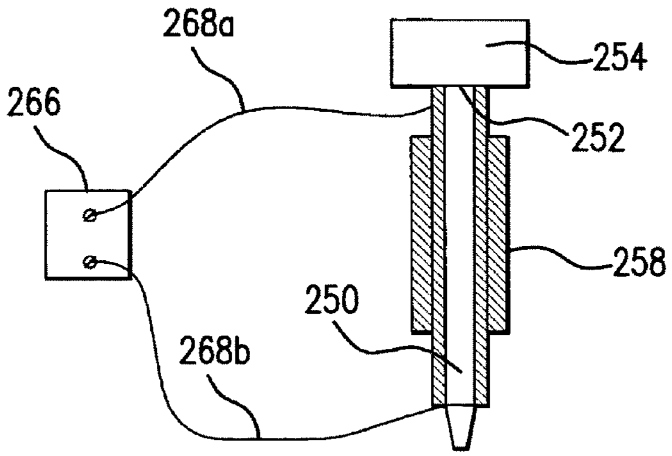
FIG. 5A shows a sectional view illustrating portions of a source material dispenser having a conduit, e.g., capillary tube, that is coated with a layer of conductive material for heating the conduit.

FIG. 5A shows portions of a source material dispenser producing source material droplets for an EUV light source including a source material conduit, which, for the case shown, includes a glass capillary tube 250 having a source material receiving end 252 that is rigidly affixed to dispenser portion 254, e.g., flange or open face seal, e.g. VCR seal component. This affixment may be achieved by brazing, bonding, e.g., epoxying, use of a CTE matched joining metal (see FIG. 3 and corresponding description provided above), or by one of the coupling arrangements shown in FIGS. 3A-3F and described above. FIG. 5A also shows that the capillary tube 250 is formed with a source material exit end 256 and that the dispenser may include an electro-actuatable element 258, e.g., piezoelectric modulator, (operable to deform the wall of the capillary tube 250 and modulate a release of source material from the dispenser).

Figure 5B:
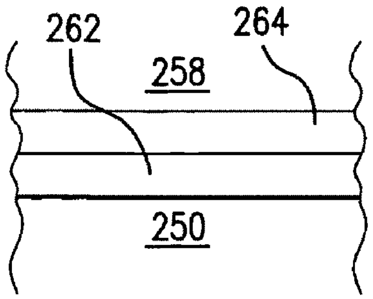
FIG. 5B shows a sectional view illustrating a conduit wall that is coated with a layer of conductive material for heating the conduit and a layer of insulating material.

As shown in FIG. 5B, a conductive coating layer 262 may be deposited to overlay, and in some cases, contact the wall of the capillary tube 250, and an insulating coating 264 may be interposed between the conductive coating layer 262 and the electro-actuatable element 258. For example, the insulating coating 264 may be deposited to overlay, and in some cases, contact the conductive coating.

FIGS. 5A and 5B illustrate that an electrical current source 266 may be placed in an electrical circuit with the conductive coating layer 262 via conductors 268*a,b* (e.g., wires) allowing a current to be passed through the conductive coating to produce heat via ohmic heating. In the configuration shown in FIG. 5A, electrical energy is delivered to the capillary with conductor 268*a* connected to layer 262 at the tip of the capillary tube 250 and conductor 268*b* connected to layer 262 at the base of the electro-actuatable element 258. With this arrangement, the upper portion of the capillary 250 may be heated by conduction through the metal dispenser portion 254. The conductors 268*a,b* may be attached to the layer 262 by brazing, soldering, e.g. with a high melting point alloy, or bonded, e.g., with a high temperature conductive epoxy.

For the arrangement shown, liquid Sn may be employed as the source material flowing through the capillary tube 250 at elevated temperatures, e.g., about 250 degrees C. Heating the capillary tube 250 may increase flow and prevent clogging due to solidification. In one arrangement, the capillary tube 250 may be made of glass, the conductive coating layer may consist of molybdenum or a nickel-cobalt-ferrous alloy, e.g., Kovar, and the insulating coating may consist of a metal oxide. For the source material dispenser, the electro-actuatable element 258 may be made of a piezoelectric material, an electrostrictive material, or a magnetostrictive material.

In addition to supplying electrical current to heat the capillary tube 250, the conductor 268*b* may support for the tip of the capillary tube 250 and, in turn, increase the pointing stability of the target material stream exiting the capillary tube 250. The material of the conductive layer 262 may be selected to meet the following requirements: high resistance; thermal expansion coefficient very close to that of glass; good adhesion to glass surface; high melting temperature. Materials such as nickel-cobalt-ferrous alloys, e.g., Kovar, molybdenum and tungsten, have a thermal expansion coefficient of ~4-6 ppm/K, which is fairly close to that of the borosilicate glass (8-10 ppm/K), and can be used for high temperature applications in combination with glass. Moreover, the resistivity of nickel-cobalt-ferrous alloys, e.g., Kovar, is about $4.9\cdot10^{-7}\ \Omega\cdot m$ and that of the molybdenum is about $5.34\cdot10^{-8}\ \Omega\cdot m$. Thus, a 5 μm thick layer of a nickel-cobalt-ferrous alloy, e.g., Kovar, deposited on a 1 mm capillary tube 250 with a 40 mm length, would have a suitable resistance for heating the capillary tube 250 of about 1.24Ω.

The deposition of the conductive layer 262 on the glass surface of the capillary tube 250 may be done (for example) by vacuum arc deposition using the required metal as anode material. A relatively thin (1-2 μm) insulator layer 264 (e.g., metal oxide) can be deposited on the conductive layer 262 for isolation inner electrode of the electro-actuatable element 258 e.g., piezoelectric tube. With this arrangement, the temperature of capillary tube 250 may be higher than the temperature of electro-actuatable element 258, e.g., piezoelectric tube that typically requires lower operation temperature. Higher temperatures may lead to a faster depoling of the piezoelectric materials and a larger thermal stress. Although an insulating coating is described herein, it is to be appreciated that other insulators, e.g. non-coatings, may be used to isolate the electro-actuatable element 258 from the conductive layer 262.

Figure 6:
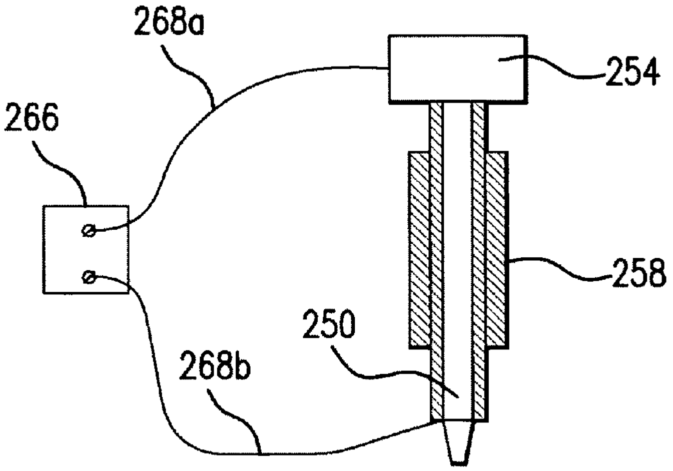
FIG. 6 shows a sectional view illustrating portions of a source material dispenser having a conduit, e.g., capillary tube, that is coated with a layer of conductive material for heating the conduit, and an arrangement in which current is passed through a conductive conduit portion and the conductive coating to heat the conduit.

FIG. 6 shows portions of another embodiment of a source material dispenser producing source material droplets for an EUV light source having one or more elements in common with the arrangement shown in FIG. 5A and described above, including a source material conduit, which, for the case shown, includes a glass capillary tube 250 having coating layers 262, 264 (as described above with reference to FIG. 5B), rigidly affixed to dispenser portion 254, an electro-actuatable element 258, an electrical current source 266, and conductors 268*a,b* (e.g., wires), allowing a current to be passed through the conductive coating 262 to produce heat via ohmic heating. In the configuration shown in FIG. 6, the dispenser portion 254 may be made of a conductive material, the conductive coating 262 may be placed in contact with the dispenser portion 254, e.g., by removal of the insulation coating 264 from portions of the capillary tube 250. With this arrangement, electrical energy can be delivered to the capillary with conductor 268*a* connected to dispenser portion 254 and conductor 268*b* connected to layer 262 at the base of the electro-actuatable element 258.

Figure 7:
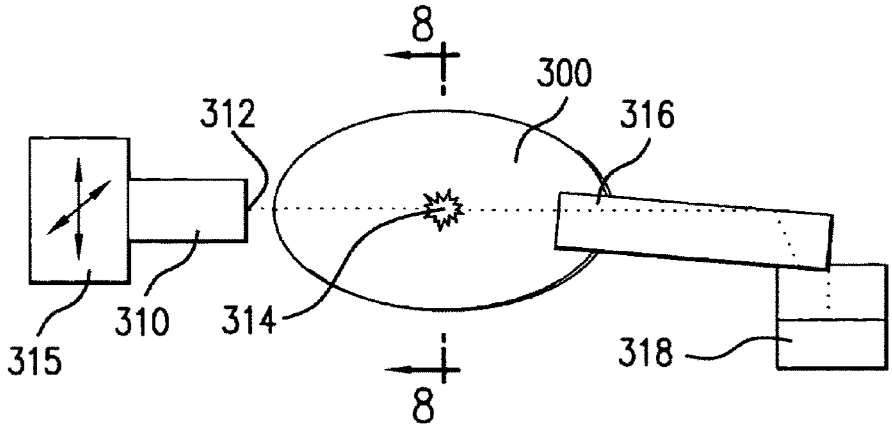
FIGS. 7-10 are views illustrating a reflective optic having a surface of revolution that defines a rotation axis and a circular periphery, the optic positioned to incline the axis at a nonzero angle relative to a horizontal plane and to establish a vertical projection of the periphery in the horizontal plane, with the periphery projection bounding a region in the horizontal plane, and having a target material release point that is located in the horizontal plane and outside the region bounded by the periphery projection (note.
Figure 8:
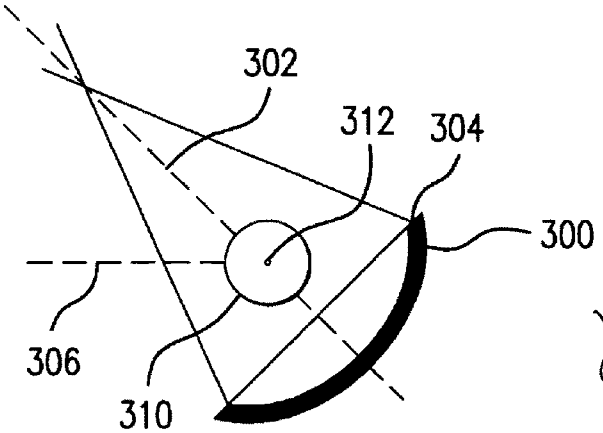
Figure 10:
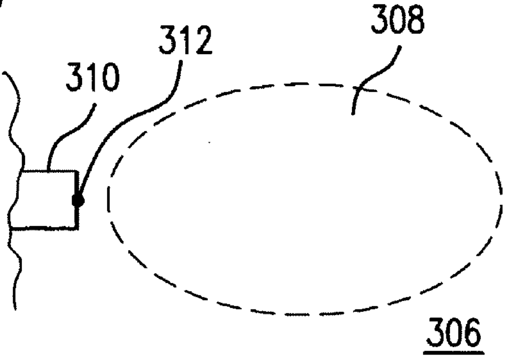
Figure 9:
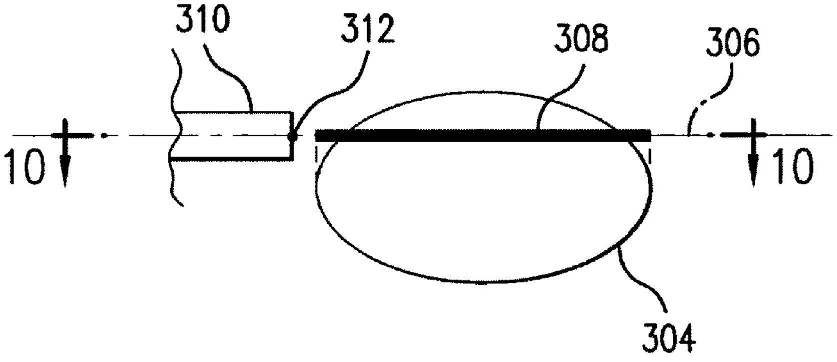

Referring now to FIG. 7, a device is shown having an EUV reflective optic 300, e.g., a near-normal incidence collector mirror having a reflective surface in the form of a rotated ellipse having, e.g., a graded multi-layer coating with alternating layers of Molybdenum and Silicon, and in some cases, one or more high temperature diffusion barrier layers, smoothing layers, capping layers and/or etch stop layers. As best seen in FIG. 8, the optic 300 is formed with a reflective surface-of-revolution that defines a rotation axis 302 and a circular periphery 304. As shown in FIGS. 7 and 8, the optic 300 may be positioned to incline the rotation axis 302 at a nonzero angle, e.g., 10-90 degrees, relative to a horizontal plane 306. FIGS. 9 and 10 illustrate that a vertical projection of the periphery 304 in the horizontal plane 306, and show that the periphery projection may bound a region 308 in the horizontal plane 306. FIGS. 7-10 also show that the device may further include a system delivering target material 310, e.g., a stream of target material droplets, the system having a target material release point 312, that is located in the horizontal plane 306 and outside the region 308, bounded by the periphery projection. A system generating a laser beam (see FIG. 1) may also be provided for irradiating the target material at an irradiation region 314 (see FIG. 7) to generate an EUV emission.

With this arrangement, EUV light is directed from the optic 300 along an axis 302 that is inclined relative to the horizontal. As indicated above, this orientation may be desirable in some cases. Also, this arrangement allows for a non-vertical droplet stream to the used, which, in some cases, may reduce optic 300 contamination relative to a vertical droplet stream. In particular, target material that is emitted from the droplet generator at very small velocities (i.e., in a case of accidental leaking of the droplet generator) would not be pulled towards the EUV collector by the force of gravity and the probability of the collector contamination would be significantly reduced. Additionally, vertically-oriented droplet streams and the supporting devices may result in vertically-oriented obscurations of the collector mirror. Depending on the design of the following EUV optics this may be a less favorable orientation of obscurations for the performance of the optics.

In this configuration, with the droplet generator positioned outside of the projection of the collector optic on the horizontal plane, droplets produced by the generator with velocity v in the horizontal direction are deflected in the vertical direction from the original path at a distance from the droplet generator L by the amount d that is given by:

$$d = \frac{g}{2}\left(\frac{L}{v}\right)^2,$$

where g is the gravitational acceleration. Thus, for a droplet velocity of 20 m/s and a distance from the droplet generator of L=30 mm the deviation from the horizontal direction d is only 1.1 mm. Therefore, for practical droplets velocities, the droplets launched in the horizontal direction would arrive to the plasma point almost in a straight horizontal line. Similar arguments can be applied to the other non-vertical orientations of the droplet generator.

As shown in FIG. 7, the system delivering target material 310 can be mounted on a steering mechanism 315 capable of tilting the system delivering target material 310 in different directions to adjust the position of the droplets, with respect to the focal point of the collector mirror, and may also translate the droplet generator in small increments along the stream axis. As further shown in FIG. 7, the droplets that are not used for the creation of plasma and the material exposed to the laser irradiation and deflected from the straight path are allowed to travel some distance beyond the irradiation region 314 and are intercepted by a catch, which for the case shown includes a structure, e.g. elongated tube 316 (having a cross section that is circular, oblong, oval, rectangular, square, etc. . . . ). In more detail, elongated tube 316 may be positioned to receive target material that has passed through the irradiation region and prevent received material from splashing and reaching the reflective optic. In some cases, the effects of splashing may be reduced/prevented by using a tube having a relatively large aspect ratio L/W, e.g. greater than about 3, where L is the tube length and W is the largest inside tube dimension normal to L. Upon striking the inner wall of the tube 316, the target material droplet lose their velocity and the target material may then be collected in a dedicated vessel 318, as shown.

Figure 11:
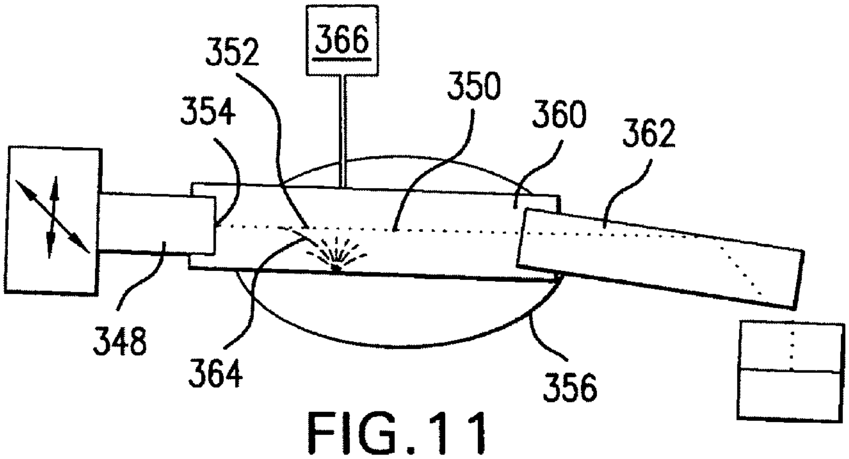
FIG. 11 is a side plan view of a device having a source of target material droplets delivering target material to an irradiation region along a non-vertical path and a catch positioned to receive target material straying from the path.

Referring now to FIG. 11, a device is shown having a source of target material droplets 348 delivering target material to an irradiation region 350 along a non-vertical path 352 between the irradiation region 350, and a target material release point 354. As shown, the device may also include an EUV reflective optic 356, (e.g., as described above for optic 300) and a first catch, which for the embodiment shown includes tubes 360, to receive target material straying from the path, e.g. material along path 364 and a second catch, which for the case shown includes a structure, e.g. elongated tube 362 positioned to receive target material that has passed through the irradiation region and prevent the received material from splashing and reaching the reflective optic.

Also shown in FIG. 11, a mechanism 366, e.g. a motorized arm, may be provided for moving the tube 360 from a position wherein the tube 360 is located along the path 352 to a position where the tube 360 does not obstruct EUV light reflected from the EUV reflective optic. In use, the tube 360 may be placed as shown during droplet startup and/or alignment and/or droplet termination, and removed, e.g. using motorized arm mechanism 366 prior to droplet irradiation.

Figure 12:
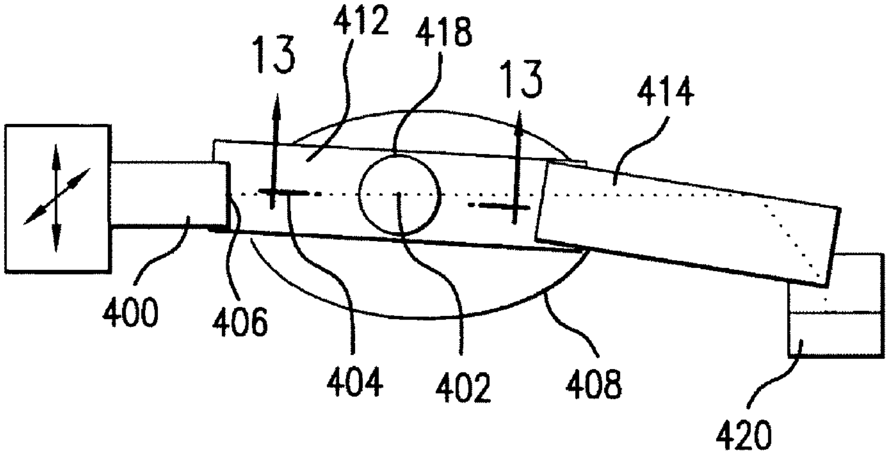
FIG. 12 is a side plan view of a device having a source of target material droplets delivering target material to an irradiation region along a non-vertical path, a first catch in the form of a shield positioned to receive target material straying from the path, wherein the shield may remain in position during target material irradiation and a second catch in the form of a structure positioned to receive target material that has passed through the irradiation region and designed to prevent received material from splashing and reaching the reflective optic.
Figure 13:
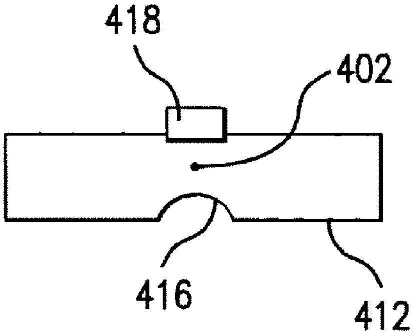
FIG. 13 shows a sectional view as seen along line 13-13 in FIG. 12 showing the catch is formed with an orifice.

FIGS. 12 and 13 illustrate a device having a source of target material droplets 400 delivering target material to an irradiation region 402 along a non-vertical path 404 between the irradiation region 402 and a target material release point 406. As shown, the device may also include an EUV reflective optic 408, (e.g. as described above for optic 300) and a first catch, which for the embodiment shown includes tube 412 to receive target material straying from the path, e.g. material along path 364 and a second catch, which for the case shown includes a structure, e.g. elongated tube 414 positioned to receive target material that has passed through the irradiation region and prevent the received material from splashing and reaching the reflective optic.

FIGS. 12 and 13 illustrate that the tube 412 may be positioned such that the irradiation region 402 is located in the tube 412, and FIG. 13 shows that the tube 412 may be formed with an orifice 416, allowing the laser beam irradiating the target material to pass into the tube 412 to the irradiation region, and to allow the EUV light generated within the tube 412 to exit the tube 412 to reach the optic 408. For this arrangement, the tube 412 may be permanently installed on the system, (i.e., may remain in the position shown in FIG. 12 during target material irradiation). In addition, a laser beam dump 418 can be attached to or integrally formed with the tube 412 on the side of the tube 412 opposite to the orifice 416, as shown. Also shown, one or both of the tubes 412, 414, may be slightly inclined relative to the horizontal direction to allow gravity to evacuate the target material accumulated in the catch. A collection reservoir 420 positioned to receive target material from the tube 414 may also be provided, as shown.

Parts, or all of the first and second catches, shown in FIGS. 12 and 13, may have double wall tubes, and the space between the tube walls may be filled with, or designed to pass one or more heat exchange fluids, such as water, tin, gallium, tin-gallium alloy, etc., for the efficient thermal management of the catch. Parts, or all of each catch, and/or reservoir, may be heated to keep the target material above its melting point to provide easy transportation to the collecting reservoir and/or to avoid clogging of the catch by the target material deposits. It may also be advantageous for a catch to be indirectly heated by the energy emitted from the plasma and/or by thermal contact with the droplet generator or the heated droplet reservoir to facilitate the transportation of (used) target material to the droplet reservoir. Materials for construction of the catch tubes 412, 414, may include, but is not necessarily limited to, titanium, tungsten and/or molybdenum due to their compatibility (no reaction), with most target materials and their relatively high melting temperature. The diameter of the catch tube 412 may be, for example, in the range of 20 mm to 100 mm with a typical wall thickness of about 1 mm to 3 mm. The catch tubes may have a circular, oval, oblong, elliptical, square, rectangular or other shape in cross-section. The orifice 416 for plasma emission, and pump laser beam input, may be sized and shaped such that it provides little or no obscuration for the EUV emission from the plasma to the outer edge of the collector optic 408, i.e., designed to match or exceed the acceptance angle of the collector optic 408.

Figure 14:
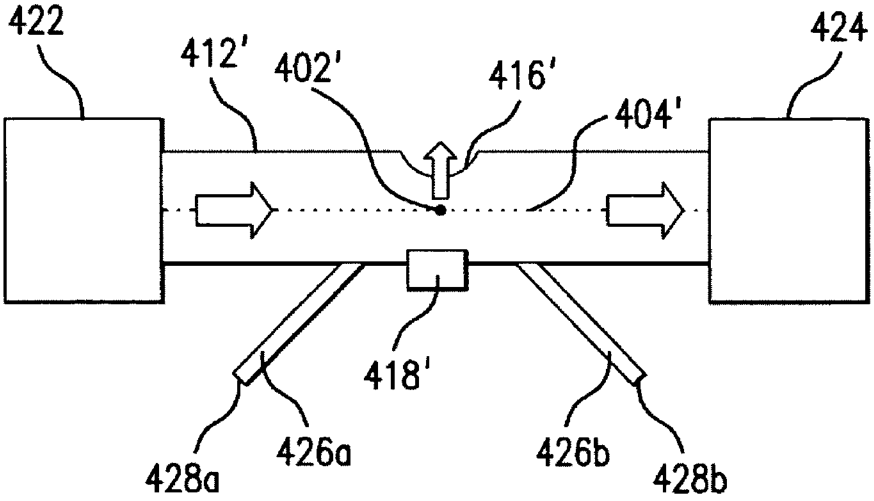
FIG. 14 is a side plan view of a device having a source of target material droplets delivering target material to an irradiation region along a non-vertical path and a catch in the form of a shield positioned to receive target material straying from the path, and including a system for flowing a gas through the catch.

FIG. 14 shows another embodiment in which the catch includes a tube 412' to receive target material straying from the path 404' and/or passing through the irradiation region 402'. FIG. 14 illustrates that the tube 412' may be positioned such that the irradiation region 402' is located in the tube 412' and that the tube 412' may be formed with an orifice 416' allowing a laser beam irradiating the target material to pass into the tube 412' to the irradiation region, and to allow the EUV light generated within the tube 412' to exit the tube 412'. For this arrangement, the tube 412' may be permanently installed on the system, (i.e. may remain in the position shown in FIG. 12 during target material irradiation). In addition, a laser beam dump 418' can be attached to, or integrally formed with, the tube 412' on the side of the tube 412' opposite to the orifice 416', as shown.

FIG. 14 further shows that a system for passing one or more gasses through the tube 412', e.g. buffer gasses, etchant gases, etc. such as $H_2$, He, Ar, HBr, HCl or combinations thereof, may be provided. As shown, this system may include a gas source 422 supply gas to the tube 412', and in some cases, an optional pump 424, e.g. vacuum pump, removing gas from the tube may be provided. One or more relatively narrow diagnostic tubes 426*a,b* (that may be sealed off at the ends 428*a,b*) may be attached to the tube 412' to allow the access to the plasma and/or droplets by one or more diagnostic instruments (not shown).

The pump opening may be larger in diameter compared to the EUV emission orifice 416'. With this arrangement, the gas may be introduced fairly close to the plasma location and (partially) directed towards the EUV emission orifice and pumped out (or circulated in a recirculation loop), rather efficiently since there may be a pressure gradient of gas from the orifice 416' to the remainder of the chamber. A lower pressure may be maintained outside of the catch tube 412' in the main part of the EUV source chamber. This reduces the amount of EUV absorption by chamber background gas. The region of highest gas pressure is limited to a fairly small volume around the gas inlet, the plasma and the catch tube(s). With respect to gas flow, the arrangement may be optimized such that the opening(s) for pumping is/are maximized in throughput (i.e., diameter), whereas the opening for EUV emission (and other required openings) are minimized. At the same time, obscurations of the EUV light path by the shield/catcher tube(s), (tube diameter), and by the EUV emission opening are minimized in order to minimize the loss of EUV light by the arrangement.

Figure 15:
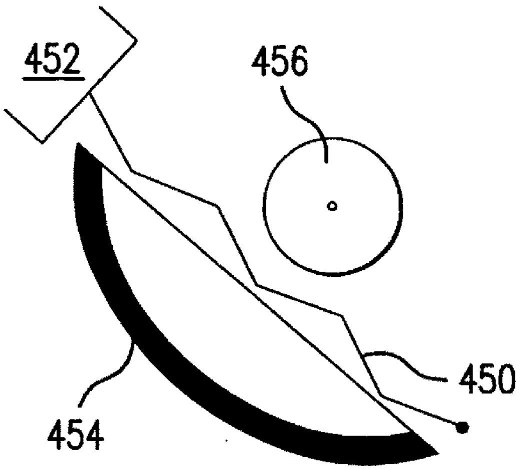
FIGS. 15 and 16 illustrate a catch that includes a cover moveable between a first extended position (FIG. 15) in which the cover is positioned over some or all of the operable surface of the reflective optic and a second retracted position (FIG. 16), in which the cover is not positioned over the reflective optic.
Figure 16:
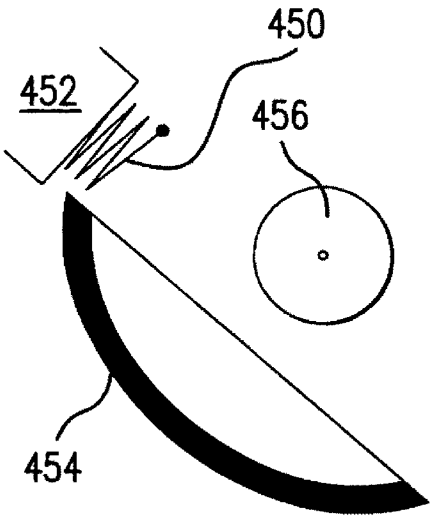

FIGS. 15 and 16 illustrate a catch that includes cover 450. Also, shown, a system 452 may be coupled to the cover 450 to extend and retract the cover 450 between a first extended position (FIG. 15), in which the cover 450 is positioned over some or all of the operable surface of the reflective optic 454, and a second retracted position (FIG. 16), in which the cover 450 is not positioned over the reflective optic 454. With this arrangement, the cover 450 may be deployed, e.g. during startup, stopping and/or device maintenance to protect the optic 454 from stray droplets/target material released from the system delivering target material 456.

Figure 17:
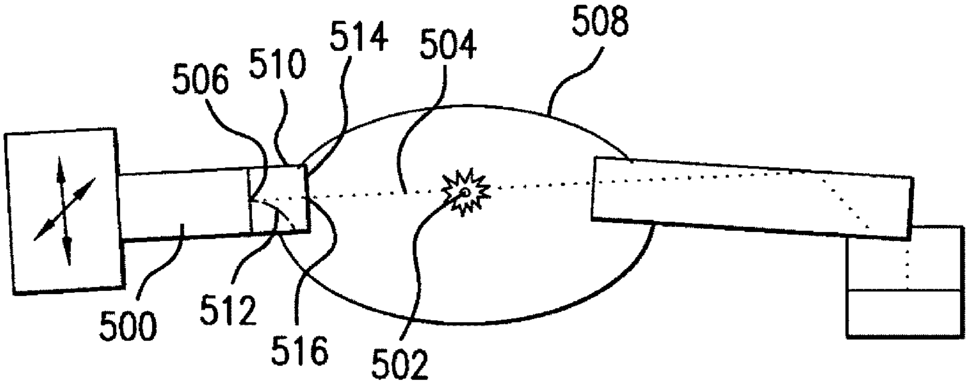
FIG. 17 is a side plan view of a device having a source of target material droplets delivering target material to an irradiation region along a non-vertical path and a catch in the form of a shield positioned to receive target material straying from the path, the shield including a tube that extends from a location wherein the tube at least partially surrounds the target material release point to a tube terminus positioned between the release point and the irradiation region.

FIG. 17 shows a device having a source of target material droplets 500 delivering target material to an irradiation region 502 along a non-vertical path 504 between the irradiation region 502 and a target material release point 506. As shown, the device may also include an EUV reflective optic 508, (e.g., as described above for optic 300) and a catch, which for the embodiment shown includes tube 510 to receive target material straying from the desired path, e.g., material along path 512. In use, the tube 510 may remain in position during irradiation of target material to generate EUV light (i.e., may remain installed during normal light source operation).

As further shown, a tube 510 may extend from a location wherein the tube at least partially surrounds the target material release point 506 to a tube terminus 514 that is positioned between the release point 506 and the irradiation region 502. Also shown, the tube 510 may have a closed end at the terminus that is formed with an opening 516 centered along the desired path 504. With this arrangement, target material traveling along the path 504 will exit tube 510, while target material straying from path 504 will be captured and held in closed-end tube 510.

Figure 18:
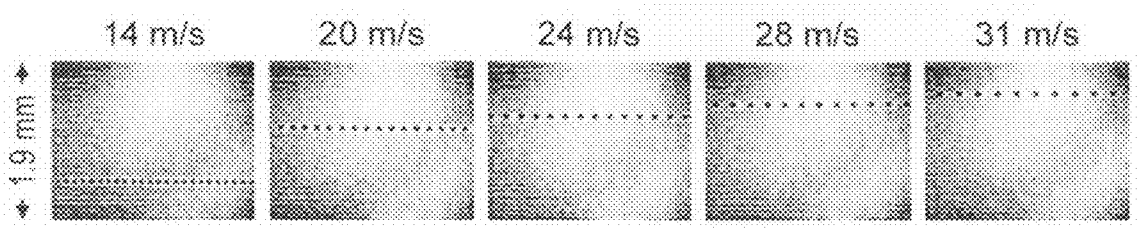
FIGS. 18 and 19 are images of non-vertical droplet streams taken at a distance of ~300 mm from a target material release point.
Figure 19:
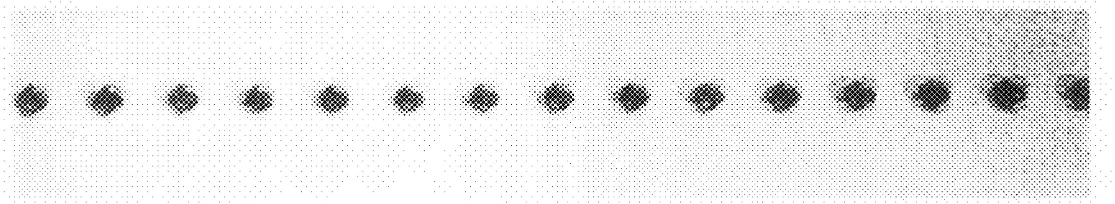

Referring now to FIGS. 18 and 19, for some light source arrangements, droplet generators may be needed to produce droplet targets of about 10-100 μm in size and at a relatively high repetition rate, e.g. 50 kHz, or higher. In some cases, droplet velocity is one of the parameters that can be used to optimize the conditions at the LPP plasma. For example, a droplet velocity from about 20 to 100 m/s, or higher, may be used. FIG. 18 shows images of horizontal droplet streams, and, in particular, shows images of tin droplets ejected in horizontal orientation with different velocities. Only a small vertical displacement (~1 mm) as a function of the droplet velocity was observed in this experiment. The droplets were produced at about 80 kHz and the pictures were taken at a distance of about 300 mm from the nozzle. The gravity-related vertical displacement d of droplets travelling with a velocity v at a distance L from the nozzle can be found as:

$$d=g/2(L/v)^2,$$

where g is the vertical acceleration due to gravity. Thus, for instance, the droplets traveling at 20 m/s would be shifted by only ~1.1 mm from the horizontal path at a 300 mm distance from the nozzle. The images shown in FIG. 18 confirm the estimates of the vertical displacement and suggest only a minor dependence of the droplet stream position on droplet velocity. This shows that it may be a viable droplet orientation for the EUV LPP source, from the point of view of matching the target position with the focused $CO_2$ laser beam.

One study of tin droplets produced in a horizontal direction indicated that a non-vertical orientation droplet stream may have little effect on the properties of the droplets. FIG. 19 shows the superposition of a large number of images of 100 μM droplets that were acquired over a time interval of 30 minutes. The images were taken at a distance of ~300 mm from the droplet generator nozzle. The droplets velocity in this experiment was 30 m/s. Very good long-term stability of the droplets can be implied from FIG. 19. The maximum vertical displacement of the droplets was ±50 μm which may be compensated by a steering system with active stabilization. On the other hand, the short-term positional stability of the droplets in horizontal orientation was on the order of 10 μm, comparable to the characteristics of the droplets produced in the vertical orientation.

While the particular embodiment(s) described and illustrated in this patent application in the detail required to satisfy 35 U.S.C. §112, are fully capable of attaining one or more of the above-described purposes for, problems to be solved by, or any other reasons for, or objects of the embodiment(s) described above, it is to be understood by those skilled in the art that the above-described embodiment(s) are merely exemplary, illustrative and representative of the subject matter which is broadly contemplated by the present application. Reference to an element in the following Claims in the singular, is not intended to mean, nor shall it mean in interpreting such Claim element "one and only one" unless explicitly so stated, but rather "one or more". All structural and functional equivalents to any of the elements of the above-described embodiment(s) that are known, or later come to be known to those of ordinary skill in the art, are expressly incorporated herein by reference and are intended to be encompassed by the present Claims. Any term used in the Specification and/or in the Claims, and expressly given a meaning in the Specification and/or Claims in the present Application, shall have that meaning, regardless of any dictionary or other commonly used meaning for such a term. It is not intended or necessary for a device or method discussed in the Specification as an embodiment, to address or solve each and every problem discussed in this Application, for it to be encompassed by the present Claims. No element, component, or method step in the present disclosure is intended to be dedicated to the public regardless of whether the element, component, or method step is explicitly recited in the Claims. No claim element in the appended Claims is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A device comprising:

an EUV reflective optic having a surface of revolution defining a rotation axis and a circular periphery, the optic positioned to incline the axis at a nonzero angle relative to a horizontal plane and to establish a vertical projection of the periphery in the horizontal plane, said periphery projection bounding a region in said horizontal plane;

a system delivering target material, said system having a target material release point, said release point located in said horizontal plane and outside the region bounded by said periphery projection; and a system generating a laser beam for irradiating said target material to generate an EUV emission.

2. A device as recited in claim 1 wherein said surface of revolution is a rotated ellipse, the ellipse defining a pair of foci and being rotated about an axis passing through each focus.

3. A device comprising:

a source of target material droplets delivering target material to an irradiation region along a non-vertical path between the irradiation region and a target material release point;

an EUV reflective optic;

a laser producing a beam irradiating droplets at the irradiation region to generate a plasma producing EUV radiation; and a catch positioned to receive target material to protect the reflective optic.

4. A device as recited in claim 3 wherein said catch comprises a tube.

5. A device as recited in claim 4 wherein said irradiation region is located in said tube and said tube is formed with an orifice to pass said EUV radiation from said irradiation region to said reflective optic.

6. A device as recited in claim 4 further comprises an in-situ mechanism for moving said tube from a position where said tube is located along said path to a position where the tube does not obstruct EUV light reflected from the EUV reflective optic.

7. A device as recited in claim 4 wherein said tube is a shield protecting the reflective optic from target material straying from the non-vertical path.

8. A device as recited in claim 7 wherein said tube extends from a location wherein the tube at least partially surrounds the target material release point to a tube terminus positioned between said release point and said irradiation region.

9. A device as recited in claim 3 wherein said catch comprises a retractable cover extendable over an operable surface of said reflective optic.

10. A device as recited in claim 3 wherein said catch comprises a structure positioned to receive target material that has passed through the irradiation region and prevent received material from splashing and reaching the reflective optic.

11. A device as recited in claim 10 wherein said structure comprises an elongated tube.

12. A source material dispenser for an EUV light source, said dispenser comprising:

a source material conduit having a wall and formed with an orifice;

a conductive coating deposited on said wall;

an insulating coating deposited on said conductive coating;

a source passing electrical current through said conductive coating to produce heat; and an electro-actuatable element contacting said insulating coating and operable to deform said wall and modulate a release of source material from said dispenser.

13. A dispenser as recited in claim 12 wherein said conduit comprises a tube.

14. A dispenser as recited in 13 wherein said tube is made of glass and said conductive coating comprises a nickel-cobalt-ferrous alloy.

15. A dispenser as recited in claim 12 wherein said insulating coating comprises a metal oxide.

16. A dispenser as recited in claim 12 wherein said electro-actuatable element is selected from a group of elements consisting of a piezoelectric material, an electrostrictive material and a magnetostrictive material.

17. A dispenser as recited in claim 12 wherein said source material comprises liquid Sn.

18. A source material dispenser for an EUV light source, said dispenser comprising:

a source material conduit comprising a tubular glass portion having a coefficient of thermal expansion ($CTE_{glass}$) and a metal coupled to the glass portion, the metal having a coefficient of thermal expansion ($CTE_{metal}$) which differs from $CTE_{glass}$ by less than 5 ppm/degree Celsius over the range of temperatures of 25 to 250 degrees Celsius.

19. A dispenser as recited in claim 18 wherein said joining metal comprises a nickel-cobalt-ferrous alloy.

20. A dispenser as recited in claim 18 wherein said joining metal comprises molybdenum.

21. A source material dispenser producing source material droplets for an EUV light source, said dispenser comprising:

a source material conduit having a source material receiving end and a source material exit end; and a confining structure restricting movement of said source material exit end of the conduit to reduce droplet stream instabilities.

22. A dispenser as recited in claim 21 wherein said source material comprises molten material heated above twenty five degrees Celsius and said confining structure comprises a rigid member sized to provide a gap between the conduit and member at the operating temperature of the conduit.

23. A dispenser as recited in claim 22 wherein said member is a ferrule made of a material having a coefficient of thermal expansion ($CTE_{ferrule}$), said conduit is made of a material having a coefficient of thermal expansion ($CTE_{conduit}$) such that a gap distance between the ferrule and conduit decreases with increasing temperature.

24. A dispenser as recited in claim 22 wherein said member is a ferrule made of a material having a coefficient of thermal expansion ($CTE_{ferrule}$), said conduit is made of a material having a coefficient of thermal expansion ($CTE_{conduit}$) such that a gap distance between the ferrule and conduit increases with increasing temperature.

25. A dispenser as recited in claim 21 wherein said confining structure comprises a flexible ferrule sized to be in contact with the conduit at the operating temperature of the conduit.

* * * * *